United States Patent [19]
Cook et al.

[11] Patent Number: 5,564,663
[45] Date of Patent: Oct. 15, 1996

[54] TRANSITIONAL PIVOT JOINT FOR HEAD SUPPORT BASE UNIT

[75] Inventors: William J. Cook; Charles Dinkler, both of Cincinnati, Ohio

[73] Assignee: Ohio Medical Instrument Company, Inc., Cincinnati, Ohio

[21] Appl. No.: 500,583

[22] Filed: Jul. 11, 1995

[51] Int. Cl.[6] ............................................. A47K 1/00
[52] U.S. Cl. .................................. 248/222.12; 5/622
[58] Field of Search .......................... 248/222.12, 228.2, 248/230.2, 313, 316.1, 316.2, 110, 251, 292.13; 297/408; 602/18; 5/622

[56] References Cited

U.S. PATENT DOCUMENTS

| | | |
|---|---|---|
| 1,618,851 | 2/1927 | Thunberg et al. . |
| 3,082,643 | 3/1963 | Grassi et al. . |
| 3,096,453 | 7/1963 | Behar . |
| 3,378,273 | 4/1968 | Lewis et al. . |
| 4,026,605 | 5/1977 | Emmerich . |
| 4,108,426 | 8/1978 | Lindstroem et al. . |
| 5,147,287 | 9/1992 | Jewell et al. ............................ 5/622 X |
| 5,177,823 | 1/1993 | Riach ..................................... 5/622 X |
| 5,221,111 | 6/1993 | Younger . |
| 5,254,079 | 10/1993 | Agbodoe et al. . |
| 5,276,927 | 1/1994 | Day ............................................ 5/622 |
| 5,318,509 | 6/1994 | Agbodoe . |
| 5,326,186 | 7/1994 | Nyberg . |

*Primary Examiner*—Ramon O. Ramirez
*Attorney, Agent, or Firm*—Wood, Herron & Evans, P.L.L.

[57] ABSTRACT

A base unit for mounting a head support to a medical table wherein a generally U-shaped frame of the base member is mounted with respect to the table. A transitional member has a first end adapted to support the head support and a shaft extending from a second end. A base clamp is mounted on the generally U-shaped frame and has a bore sized and shaped to receive the shaft of a transitional member. The shaft of the transitional member and the bore of the base clamp include a pivot joint comprised of a spring biased plunger that is located in an annular groove that together function to maintain the shaft of the transitional member at a desired axial position with respect to the bore of the base clamp.

16 Claims, 2 Drawing Sheets

TRANSITIONAL PIVOT JOINT FOR HEAD SUPPORT BASE UNIT

FIELD OF THE INVENTION

The invention relates generally to medical equipment and more particularly, to an improved, quick disconnect transitional pivot joint for a head support attached to a surgical table.

BACKGROUND OF THE INVENTION

During neurological or other procedures to the head and neck areas of a patient, it is common for the patient to lie on a table with the patient's head at or extending beyond the end of the table. A head support, designed to hold the patient's head during a surgical procedure, is mounted on a mechanical connector or "base unit" which, in turn, is attached at the end of the table. The base unit has movable elements that permit the head support to be adjusted and clamped at a position and orientation having a desired elevation and longitudinal position with respect to the table. The head support may be a skull clamp which securely and rigidly holds a patient's head in the desired position and orientation. Alternatively, the patient's head may be supported by a head rest, for example, a horseshoe-shaped head rest, or a general purpose head rest.

Typically, the head support is coupled to one end of a swivel adaptor which is an angled connector preferably providing two degrees of rotational freedom. The other end of the swivel adaptor is connected to one end of a swivel arm or transitional arm on the base unit. The transitional arm is used to change the elevation of the head support. A shaft on the other end of the transitional arm is located within a bore at one end of a base clamp. The other end of the base clamp is rotationally coupled to a frame which may be longitudinally and laterally adjusted with respect to the end of the table. Therefore, by rotationally adjusting the transitional arm with respect to the frame, and further adjusting the position of the frame relative to the table, the head support can be moved into any desired position and orientation.

In accordance with a known prior art design illustrated in FIG. 4, the end of the base clamp 10 contains a threaded hole 11, reaching to the bore 12, through which a thumb screw 13 extends. The distal end 14 of the thumb screw 13 is located in an annular groove 15 in a shaft 16 on the other end of the transitional arm 17. Therefore, the distal end 14 of the thumb screw 13 and the annular groove 15 provide a guide for the pivoting action of the transitional arm 17 with respect to the base clamp 10, and further, prevent the transitional arm 17 from separating axially from the base clamp 10. The thumb screw 13 is loosened to disengage it completely from the annular groove 15, thereby permitting the transitional arm 17 to be removed from the base clamp 10, as for cleaning. In addition, the thumb screw 13 itself may be unscrewed from the base clamp 10, so that the thumb screw 13 and its mating hole 11 in the base clamp 10 can be cleaned.

While the above design works satisfactorily, it does have several disadvantages. First, the screw 13 extends from the base clamp and is subject to being inadvertently hit or bumped. Consequently, the screw 13 is subject to being damaged or broken off in the threaded hole 11. Therefore, use of the base clamp is impeded, if not prevented, until the broken screw can be removed and replaced with a new screw. Further, the surfaces of the screw 13 which are outside the base clamp have the further disadvantage of collecting contaminants, and therefore, must be cleaned. When the screw 13 is separated from the base clamp for cleaning, it can be lost which prevents use of the base clamp until the screw is replaced.

SUMMARY OF THE INVENTION

To overcome the disadvantages noted above, an object of the present invention is to provide a quick disconnect transitional arm pivot joint with the base unit that is less susceptible to collecting contaminants, easier to clean, and does not have holes that localize stress forces.

The present invention is used in connection with a base unit for mounting a head support to a medical table. The base unit includes a transitional member which has a first end adapted to support the head support and a shaft extending from the other end. A base clamp has a bore sized and shaped to axially receive the shaft of the transition arm, According to the principles of the present invention and in accordance with the preferred embodiment, a hole is located in the shaft and forms a hole opening in an outer shaft surface. A plunger is captured in the hole and has one end protruding through the hole opening. A spring is located in the hole and biases the plunger outward through the hole opening. The base clamp has an annular groove which is sized and shaped to receive the one end of the plunger protruding through the hole opening. The one end of the plunger, when located within the annular groove, functions therewith to first, guide rotational motion between the base clamp and the transitional arm, and second, maintain the shaft of the transitional arm in its desired location with respect to the base clamp.

In another aspect of the invention, a second hole is located in the shaft and forms a second hole opening in the outer shaft surface. A second plunger is captured in the second hole and has one end protruding through the second hole opening, and a second spring is located in the second hole for biasing the second plunger outwardly through the second hole opening. In another aspect of the invention, the first and second hole openings have areas less than the cross sectional areas of the first and second holes respectively. Further, the first and second plungers have cross sectional areas less than the cross sectional areas of the first and second holes, respectively, and greater than the areas of the respective first and second hole openings. Therefore, the first and second plungers slide freely within the first and second holes, respectively, but are restrained therein by the respective first and second hole openings.

In a still further aspect of the invention, the first and second plungers are balls; and the spring further comprises first and second compression springs disposed in the first and second holes, respectively, for biasing the first and second balls against the respective first and second hole openings.

The above construction provides a quick disconnect transitional pivot joint which is free of through-holes extending into a bore at the end of the base clamp. While the bore does contain at least one annular groove, and while clamping and unclamping forces will cause stress forces to emanate from the groove, those stress forces will have less of a tendency to lead to stress fractures than the stress forces emanating from the through-hole of the prior art design. Therefore, a first advantage of the above construction is that the base clamp will have a longer and more reliable useful life. Further, since with the above construction, all of the components of the pivot joint are located within the bore of the base clamp, the external surfaces of the end of the base clamp are free of discontinuities and projections therefrom.

Therefore, the construction of the present invention has fewer parts that accumulate contaminants and require cleaning.

These and other objects and advantages of the present invention will become more readily apparent during the following detailed description together with the drawings herein.

DETAILED DESCRIPTION OF THE INVENTION

Figure 1:
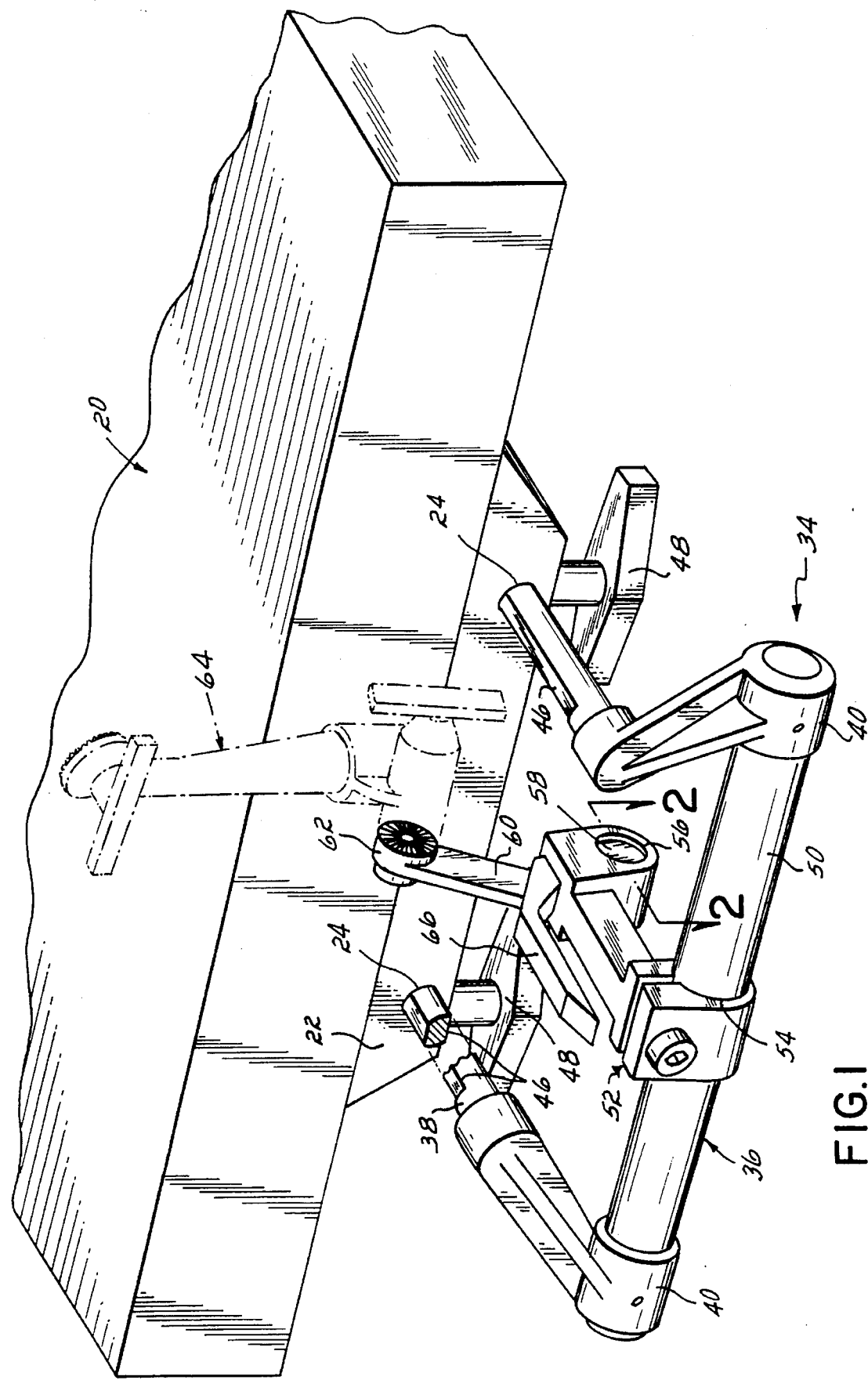
FIG. 1 is a perspective view of a base unit used with a transitional pivot joint in accordance with the principles of the present invention.

Referring to FIG. 1, a patient support member 20 of a medical table (not shown) includes a mounting plate 22 that extends longitudinally beneath the patient support member 20. The mounting plate 22 has two longitudinally extending sockets or holes 24. A base unit 34 has a generally U-shaped frame 36 with shafts 38 forming two generally parallel side legs. The shafts 38 are inserted at one end into the holes 24 of the mounting plate 22. Flats 46 on opposite sides of each of the shafts 38 are oriented such that they align with and are contacted by the screw clamps 48 on the bottom of the mounting plate 22. The screw clamps 48 extend into the bores 24 and engage the flats 46 on the shafts 38 to lock the base unit 34 at a desired longitudinal position with respect to the table 20. The U-shaped frame 36 further includes a cross bar 50 which extends between and has its ends connected to the end brackets 40. The cross bar 50 forms a base element of the U-shaped frame 36. A base clamp 52 has a first bore 54 at a first end that is sized and shaped to axially receive the cross bar 50. The base clamp 52 has a second bore 56 on an opposite end thereof which is sized and shaped to axially receive a shaft 58 on one end of a transitional link or arm 60. The other end of the transitional link 60 is coupled to a swivel adapter 64 shown in phantom, which, in turn, is coupled to a head support (not shown).

The base clamp 52 has an operating handle 66 that is operatively connected to mechanisms (not shown) within the base clamp 52 that simultaneously rigidly clamp and unclamp the bores 54, 56 to respective shafts 50, 58 in response to lowering and raising respectively, the clamp handle 66. Further, the clamp handle 66 may be moved to intermediate positions between the fully raised and the fully lowered positions which are effective to exert a proportionally lesser clamping force on the shafts 50, 58, such that the shafts 50, 58 are frictionally held, but not rigidly locked within their respective bores 54, 56. The base unit 34, including the frame 36, base clamp 52, transitional arm 60 and swivel adaptor 64 are commercially available from Ohio Medical Instruments Co., Inc. of Cincinnati, Ohio.

Figure 2:
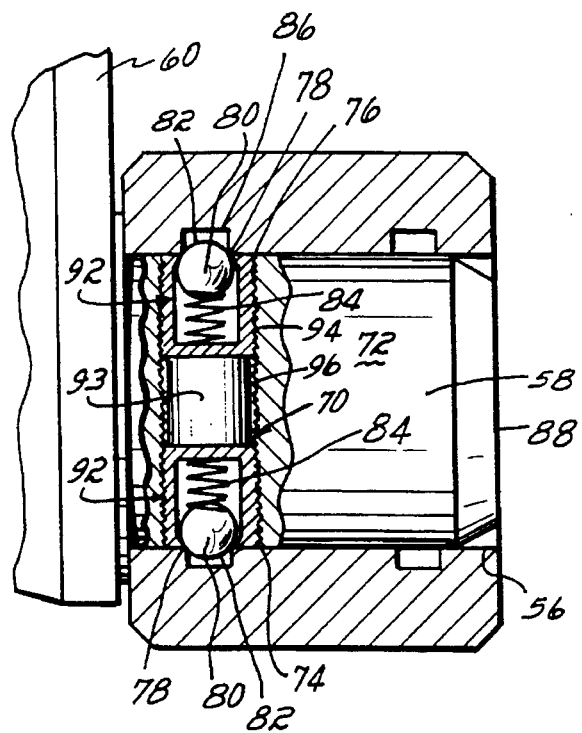
FIG. 2 is an enlarged partial cross-sectional view illustrating the pivot connection between the transitional arm and the base clamp as seen generally along line 2—2 of FIG. 1.

Referring to FIG. 2, the shaft 58 on the transitional arm 60 has a hole 70 extending diametrically therethrough and intersecting the surface 72 of the shaft 58 at two locations 74, 76. The intersection of the hole 70 with the surface 72 may form a generally circular entrance opening 78 that has a diameter and area less than the diameter and cross-sectional area of the hole 70. Balls 80 are captured within the hole 70, and the balls 80 have a diameter and cross-sectional area that is slightly less than the diameter and cross-sectional area of the hole 70 but greater than the diameter and area of the openings 78. Therefore, the balls 80 are free to slide within the hole 70 but will not pass through the openings 78. When the balls 80 are located at the ends of the hole 70, a portion 82 of the balls extends through the openings 78 and protrudes above the surface 72 of the shaft 58. Compression springs 84 are located in the hole 70. Ends of the springs 84 are in contact with and push or bias the balls 80 outwardly from the hole 70 and against a circumferential surface of the openings 78. Preferably, each of the balls 80 and an associated compression spring 84 are contained within a hollow cylindrical body 92 to form a ball and spring plunger assembly. Further, the cylindrical body 92 has external threads 94 that mate with threads 96 within the hole 70, so that the cylindrical body 92 may be screwed into the hole 70. As illustrated in FIG. 2, two cylindrical bodies 92 which make up two ball and spring detent assemblies are screwed into the hole 70 with a spacer 93 therebetween, so that the proper spacing of the balls 80 relative to the surface 72 is maintained. Such ball and spring plunger assemblies are commercially available from McMaster-Carr of Chicago, Ill.

The bore 56 within the base clamp 52 has an annular groove 86 that is positioned opposite the balls 80 when the shaft 58 is located within the bore 56 in its desired position. The annular groove 86 is sized and shaped to receive the portions 82 of the balls 80 protruding above the surface 72 of the shaft 58.

Referring to FIG. 1, in use, by sliding the shafts 38 within the bores 24, the base unit 34 and adaptor 64 are moved to a desired longitudinal position with respect to the table 20; and clamps 48 lock the base unit 34 in that position. Thereafter, the clamp handles 66 of the base clamp 52 is partially raised to slightly open the bores 54, 56 and permit the base clamp 52 to rotate on cross member 50 and the transitional arm 60 to pivot with respect to the bore 56, thereby moving arm 60 and adaptor 64 to a desired elevation. The above adjustments are repeated until the head support (not shown) is in the desired position and orientation.

As shown in FIG. 2, the portions 82 of the ball 80 that protrude above the surface 72 of the shaft 58 into the annular grooves 86 of the bore 56 guide the pivoting action of the transitional arm 60 within the bore 56. In addition, the protruding portions 82 of the balls 80 engage the annular groove 86 to prevent the shaft 58 from moving axially with respect to the axis of rotation and becoming disengaged from the bore 56. The clamps 48 and base clamp 52 are used in combination with the swivel adapter 64 to precisely position a head support such as a skull clamp or a head rest to its desired position and/or orientation.

Figure 3:
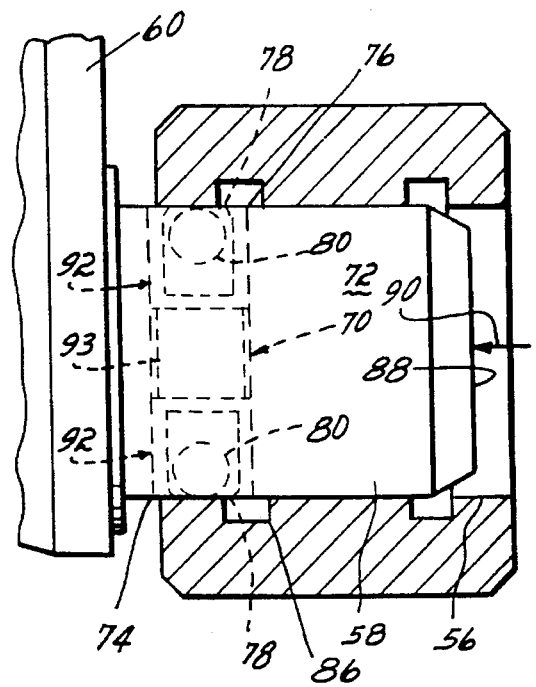
FIG. 3 is a partial cross-sectional view illustrating the pivot joint as the transitional arm is being removed from the base clamp.
Figure 4:
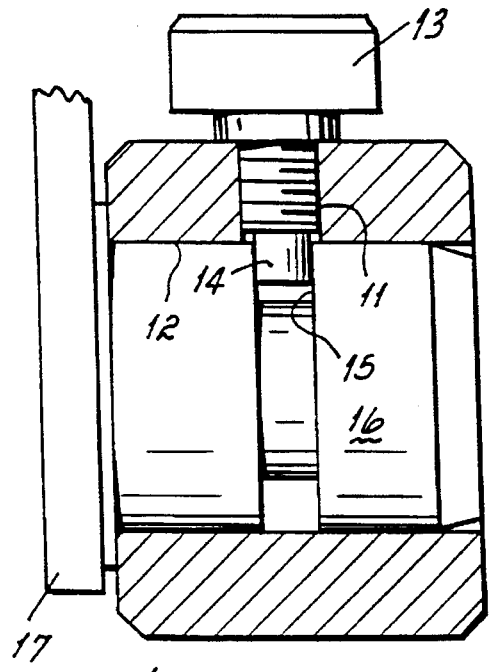
FIG. 4 is a partial cross-sectional view of a prior art pivot joint between the transitional arm and the base clamp.

At different times, it is desirable to clean the various components of the base unit 34. The swivel adapter 64 is removed from the end 62 of the transitional arm 60. To separate the transitional arm from the clamp 52, the clamp handle 66 is first raised to the position which opens the bore 56 to its maximum size, thereby unlocking and allowing the transitional shaft 58 to freely rotate within the bore 56. Referring to FIG. 3, using fingers or other manual means, a force is applied against the end 88 of the transitional shaft 58 in a direction 90 tending to separate the transitional arm 60 from the base clamp 52. That axial force is effective to create forces on the protruding portions of the balls 80 (FIG. 2) which are directed generally toward the center of the transitional shaft 58. When those forces have a magnitude that exceeds the biasing forces produced by the spring 84, the protruding portions 82 of the balls 80 are cammed or pushed into the hole 70 until they are below the surface 72 of the shaft 58. When that occurs, the transitional arm 60 and transitional shaft 58 are free to move axially within the bore 56 in the direction indicated by the arrow 90; and the transitional arm 60 may be separated from the base clamp 52 and cleaned.

The above pivot joint formed by the balls 80 biased through the openings 78 by the spring 84 and into the groove 86 of the bore 56 has the advantage of guiding motion of the transitional shaft 58 within the base clamp 52, and at the same time, preventing the transitional shaft 58 from separating from the base clamp 52. Another advantage of the pivot joint of the present invention is that the end of the base clamp has no throughholes; and therefore, the potential for stress fractures in the end of the base clamp due to a repeated clamping and unclamping action is minimized. A further advantage is that the pivot connection has fewer components that are exposed to contamination and require cleaning.

While the invention has been set forth by a description of the embodiment in considerable detail, it is not intended to restrict or in any way limit the claims to such detail. Additional advantages and modifications will readily appear to those who are skilled in the art. For example, the ball and spring assemblies described may be replaced by individual components of two balls and a compression spring extending therebetween. The balls may be held in the hole 70 by peening or otherwise forming the ends to the hole 70 to the openings 78 that have a reduced diameter. Alternatively, The balls 80 functioning as plungers may take on many other shapes and forms. For example, the balls 80 may be replaced by cylindrical elements that have a hemispherical tip on one end. Alternatively, the plunger elements 80 and mating hole 70 may be square, hexagonal or have other cross-sectional shapes. Further, the plunger elements 80 may be captured and/or restrained within its mating hole 70 by mechanisms other than a reduced area hole opening 78. For example, the plunger may have a longitudinal slot through which a pin, fixed to the shaft 58, is inserted. Therefore, the fixed pin will limit longitudinal motion of the plunger 80 within its mating hole 70. In addition, other mechanisms may be devised for limiting motion of the plunger 80 within the mating hole 70.

While the embodiment of FIGS. 2 and 3 illustrate two ball and spring plunger assemblies that are diametrically opposite each other. The pivot joint may be implemented using a fewer or greater number of ball and spring plunger assemblies. For example, a second annular groove 87 identical in size and shape to annular groove 86 can be added to the opposite end of the bore 56 of base clamp 52, thereby allowing the shaft 58 of transitional link 60 to be inserted into either end of the bore 56. Further, only one ball and spring plunger assembly can be used, or, three or more can be used. In addition, multiple ball and plunger assemblies can be axially located at different positions and intersect with multiple annular grooves in the bore of the base clamp. The invention, therefore, in its broadest aspects, is not limited to the specific details shown and described. Accordingly, departures may be made from such details without departing from the spirit and scope of the invention.

What is claimed is:

1. An apparatus for mounting a head support to a medical table comprising:

a frame adapted to be mounted with respect to the table;

an arm having
  a first end adapted to support the head support, and
  a shaft having an outer shaft surface and extending from a second end of the arm;

a first hole in the shaft forming a first hole opening in the outer shaft surface;

a first plunger captured in the first hole and having one end protruding through the first hole opening;

a first spring located in the first hole for biasing the first plunger outwardly through the first hole opening; and a clamp mounted on the frame and having
  a bore with a bore surface, the bore having a size and shape to axially receive the shaft of the arm,
  a first annular groove in the bore surface, the first annular groove having a size and shape to receive the one end of the first plunger protruding through the first hole opening, and
  the one end of the first plunger being located within the first annular groove to guide a relative rotation between the arm and the clamp and to maintain the shaft in the bore, and the one end of the first plunger being pushed out of the first annular groove in response to a force applied axially on the shaft in a direction tending to separate the arm from the clamp.

2. The apparatus of claim 1 wherein the first hole opening has an area less than a cross-sectional area of the first hole.

3. The apparatus of claim 2 wherein the plunger is sized to slide within the first hole but be restrained within the first hole by the first hole opening.

4. The apparatus of claim 3 wherein the plunger is a ball and the spring is a compression spring.

5. The apparatus of claim 1 further comprising:

a second hole in the shaft forming a second hole opening in the outer surface of the shaft;

a second plunger captured in the second hole and having one end protruding through the second hole opening; and a second spring located in the second hole for biasing the second plunger outwardly through the second hole opening.

6. The apparatus of claim 5 wherein the second hole opening has an area less than a cross-sectional area of the second hole.

7. The apparatus of claim 6 wherein the second plunger is sized to slide within the second hole but be restrained within the second hole by the second hole opening.

8. The apparatus of claim 3 wherein the first and the second plungers are first and second balls and the first and the second springs are compression springs.

9. The apparatus of claim 8 wherein the first and the second holes form a single hole extending diametrically through the shaft and the first and second balls and the first and the second springs are disposed in the single hole.

10. The apparatus of claim 9 further comprising a spacer disposed in the single hole between the first and second springs.

11. The apparatus of claim 9 wherein the first and second springs comprise a single compression spring disposed in the single hole between the first and the second balls.

12. An apparatus for mounting a head support to a medical table comprising:

a frame having
  two legs having first ends adapted to be mounted with respect to the table, and
  a cross bar connecting opposite ends of the two legs;

a transitional arm having a first end adapted to support the head support, and a shaft extending from a second end of the transitional arm, the shaft having an outer surface and a first hole intersecting the outer surface to form a first hole opening;

a first plunger captured in the first hole and having one end protruding through the first hole opening;

a spring located in the first hole for biasing the one end of the first plunger outwardly against the first hole opening; and a base clamp mounted on the frame and having a first bore at a first end of the base clamp sized to axially receive the cross bar, a second bore at a second end of the base clamp sized to axially receive the shaft of the transitional arm, the second bore having an annular groove sized to receive the one end of the plunger protruding through the hole opening, the one end of the plunger and the annular groove maintaining the shaft in the second bore, and the one end of the plunger being pushed out of the annular groove in response to a force applied axially on the shaft in a direction tending to separate the transitional arm from the base clamp, and a clamping mechanism operably connected with the first and second bores of the base clamp for selectively tightening and loosening the first bore on the cross bar and the second bore on the shaft so that the base clamp is selectively made immovable and movable, respectively, with respect to the cross bar and the shaft.

13. The apparatus of claim 12 further comprising:

a second hole intersecting the outer surface of the shaft to form a second hole opening; and a second plunger captured in the second hole and having one end protruding through the second hole opening.

14. The apparatus of claim 13 wherein the first and the second holes are diametrically aligned with respect to the shaft such that the first and the second hole openings are at diametrically opposed locations on the outer surface of the first shaft.

15. The apparatus of claim 14 wherein the first and the second hole openings have areas less than cross-sectional areas of the first and the second holes, respectively, and the first and the second plungers have cross-sectional areas less than the cross-sectional areas of the first and the second holes, respectively, and greater than the areas of the respective first and second hole openings.

16. The apparatus of claim 15 wherein the first and the second plungers are first and second balls and the spring further comprises first and second compression springs located in the first and the second holes, respectively, for biasing the first and the second balls against the respective first and the second hole openings.

* * * * *